US012639837B2

(12) United States Patent
Nakamura et al.

(10) Patent No.: US 12,639,837 B2
(45) Date of Patent: May 26, 2026

(54) SHAPE MEASUREMENT SYSTEM FOR ENDOSCOPE AND SHAPE MEASUREMENT METHOD FOR ENDOSCOPE

(71) Applicants: OLYMPUS CORPORATION, Tokyo (JP); NATIONAL CANCER CENTER, Tokyo (JP)

(72) Inventors: Tatsuya Nakamura, Tokyo (JP); Daichi Watanabe, Tokyo (JP); Kazunari Hanano, Tokyo (JP); Keigo Matsuo, Tokyo (JP); Taku Sakamoto, Tokyo (JP); Ichiro Oda, Tokyo (JP)

(73) Assignees: OLYMPUS CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 270 days.

(21) Appl. No.: 18/244,394

(22) Filed: Sep. 11, 2023

(65) Prior Publication Data

US 2023/0419517 A1     Dec. 28, 2023

Related U.S. Application Data

(63) Continuation of application No. PCT/JP2021/010118, filed on Mar. 12, 2021.

(51) Int. Cl.
*G06T 7/50* (2017.01)
*A61B 1/00* (2006.01)

(52) U.S. Cl.
CPC .............. *G06T 7/50* (2017.01); *A61B 1/0005* (2013.01); *G06T 2207/10028* (2013.01); *G06T 2207/20081* (2013.01); *G06T 2207/30096* (2013.01)

(58) Field of Classification Search
CPC ... G06T 7/50; G06T 7/62; G06T 2207/30096; G06T 2207/10068; G06T 2207/20104; A61B 1/000094
See application file for complete search history.

(56) References Cited

U.S. PATENT DOCUMENTS 6,945,931 B2 * 9/2005 Ogawa ................... A61B 1/042
                                                          600/109
7,782,453 B2 * 8/2010 Bendall ................. F01D 21/003
                                                          356/241.1
(Continued)

FOREIGN PATENT DOCUMENTS

CN     109381152 A  * 2/2019 ............... G06T 7/62
CN     107307884 B  * 11/2019 ........... A61B 8/5223
(Continued)

OTHER PUBLICATIONS

M. Liedlgruber and A. Uhl, "Endoscopic image processing—an overview," 2009 Proceedings of 6th International Symposium on Image and Signal Processing and Analysis, Salzburg, Austria, 2009, pp. 707-712, doi: 10.1109/ISPA.2009.5297635. (Year: 2009).*
(Continued)

*Primary Examiner* — Michael Robert Cammarata
(74) *Attorney, Agent, or Firm* — Scully, Scott, Murphy & Presser, P.C.

(57) ABSTRACT

A display processing unit causes a display device to display an endoscopic image of a living tissue in a somatic cavity captured by an endoscope. An operation reception unit receives a user operation that is performed so as to set an area of interest in the endoscopic image. An area-of-interest setting unit sets the area of interest in the endoscopic image based on the user operation. A three-dimensional information acquisition unit acquires three-dimensional shape information of the living tissue captured by the endoscope. A virtual surface derivation unit derives three-dimensional shape information of a virtual surface in the area of interest from three-dimensional shape information of an area different from the area of interest. A size information identification unit identifies information concerning a size of the (Continued)

virtual surface from the three-dimensional shape information of the virtual surface.

10 Claims, 16 Drawing Sheets

(56) References Cited

U.S. PATENT DOCUMENTS

| | | | | |
|---|---|---|---|---|
| 8,913,110 | B2 * | 12/2014 | Hori ........................ | H04N 7/183 |
| | | | | 348/65 |
| 9,412,054 | B1 * | 8/2016 | Krupnik .................. | A61B 1/041 |
| 9,911,203 | B2 * | 3/2018 | Krupnik ................ | G06T 7/0012 |
| 11,991,478 | B2 * | 5/2024 | Kamon ................ | A61B 1/0005 |
| 12,487,443 | B2 * | 12/2025 | Yamamoto .............. | G06T 7/593 |
| 2004/0054256 | A1 * | 3/2004 | Ogawa ............... | A61B 1/00048 |
| | | | | 600/109 |
| 2005/0052452 | A1 * | 3/2005 | Baumberg .............. | G06T 17/00 |
| | | | | 345/419 |
| 2009/0097725 | A1 * | 4/2009 | Krupnik .................. | A61B 1/041 |
| | | | | 382/128 |
| 2016/0196643 | A1 * | 7/2016 | Bendall ...................... | G06T 7/62 |
| | | | | 382/108 |
| 2019/0043188 | A1 * | 2/2019 | Wang ......................... | G06T 7/62 |
| 2019/0279380 | A1 * | 9/2019 | Bendall ................... | G06F 3/005 |
| 2020/0060528 | A1 * | 2/2020 | Akimoto ................. | G06T 7/579 |
| 2020/0301126 | A1 * | 9/2020 | Sakamoto .......... | G02B 23/2484 |
| 2022/0130105 | A1 * | 4/2022 | Sakamoto ............. | G06T 15/205 |
| 2023/0000331 | A1 * | 1/2023 | Sasaki .................. | A61B 1/0638 |
| 2023/0105799 | A1 * | 4/2023 | Nishide .................. | G16H 50/70 |
| | | | | 382/131 |

FOREIGN PATENT DOCUMENTS

| | | |
|---|---|---|
| CN | 110811491 A | 2/2020 |
| JP | 2017-023562 A | 2/2017 |
| JP | 2017-162452 A | 9/2017 |
| JP | 2018-197674 A | 12/2018 |

OTHER PUBLICATIONS

Laurentini (A. Laurentini, "The Visual Hull Concept of Silhouette-Based Image Understanding". IEEE Transactions on Pattern Analysis and machine Intelligence, vol. 16, No. 2, pp. 150-162, Feb. 1994 (Year: 1994).*

Grauman, Shakhnarovich and Darrell, "Inferring 3D structure with a statistical image-based shape model," Proceedings Ninth IEEE International Conference on Computer Vision, Nice, France, 2003, pp. 641-647 vol. 1, doi: 10.1109/ICCV.2003.1238408. (Year: 2003).*

International Preliminary Report on Patentability dated Sep. 12, 2023 and Written Opinion of the International Searching Authority dated May 18, 2021 received in PCT/JP2021/010118.

International Search Report dated May 18, 2021 received in PCT/JP2021/010118.

Chinese Office Action dated Feb. 14, 2026 received in 202180095271.8.

* cited by examiner

IMAGE-CAPTURING DIRECTION

ENDOSCOPIC IMAGE

EXAMINATION ROOM

6

DISPLAY DEVICE

12a

DISPLAY DEVICE

12b

DISPLAY DEVICE

7

5

ENDOSCOPIC OBSERVATION DEVICE

10a

INFORMATION PROCESSING DEVICE

10b

INFORMATION PROCESSING DEVICE

4

9

IMAGE STORAGE SERVER

8

IMAGE ANALYSIS DEVICE

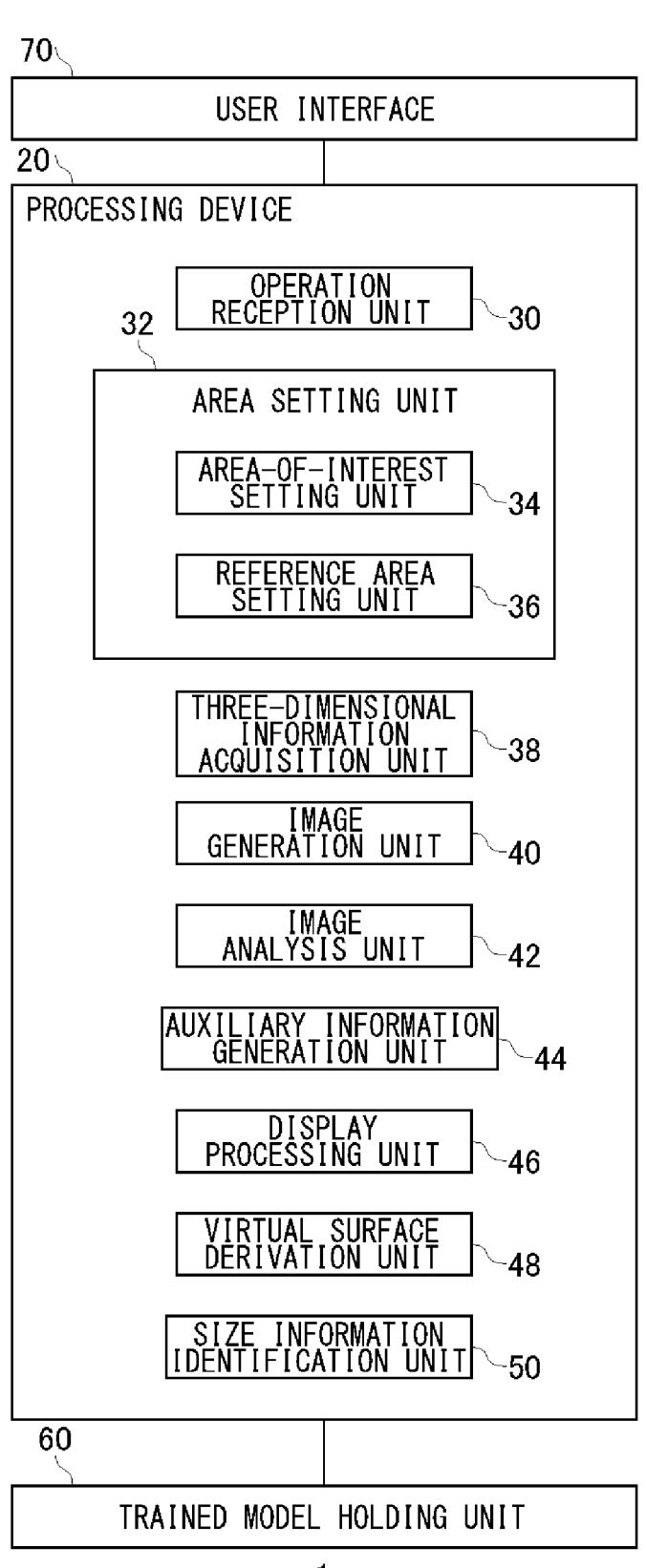

70 USER INTERFACE

20 PROCESSING DEVICE

OPERATION RECEPTION UNIT ~30

32 AREA SETTING UNIT

AREA-OF-INTEREST SETTING UNIT ~34

REFERENCE AREA SETTING UNIT ~36

THREE-DIMENSIONAL INFORMATION ACQUISITION UNIT ~38

IMAGE GENERATION UNIT ~40

IMAGE ANALYSIS UNIT ~42

AUXILIARY INFORMATION GENERATION UNIT ~44

DISPLAY PROCESSING UNIT ~46

VIRTUAL SURFACE DERIVATION UNIT ~48

SIZE INFORMATION IDENTIFICATION UNIT ~50

60 TRAINED MODEL HOLDING UNIT

1

12b

12b

12b

130

130

12b

12b

12b

SHAPE MEASUREMENT SYSTEM FOR ENDOSCOPE AND SHAPE MEASUREMENT METHOD FOR ENDOSCOPE

CROSS-REFERENCE TO RELATED APPLICATIONS

This application is based upon and claims the benefit of priority from the International Application No. PCT/JP2021/010118, filed on Mar. 12, 2021, the entire contents of which are incorporated herein by reference.

BACKGROUND

1. Field of the Disclosure

The present disclosure relates to a shape measurement system for endoscopes and a shape measurement method for endoscopes.

2. Description of the Related Art

ESD (Endoscopic submucosal dissection) is a treatment method for en bloc excision of lesions using a dedicated treatment tool, and is attracting attention as a less invasive treatment method in place of conventional surgical treatment. It is important that tumor size is accurately measured since tumors subject to ESD are lesions that are not at risk of lymph node metastasis and metastasis rates and tumor size are correlated.

Japanese Patent Application Publication No. 2017-23562A discloses a three-dimensional shape measurement device that projects a projection image of a pattern for measurement by laser light onto an observation site and calculates the three-dimensional shape of the observation site based on the image-capturing results of the pattern for measurement projected onto the observation site. Further, Japanese Patent Application Publication No. 2017-162452 discloses a technique for determining a reference surface by determining the three-dimensional coordinates of multiple points on the surface of an object in close proximity to an anomaly such as a dent, crack, or pitting.

SUMMARY

It is important to accurately measure the size of lesions such as tumors not only as a criterion when considering the implementation of ESD but also in diagnosis through endoscopic observation. However, an inner wall of a digestive tract has a curved shape, and no method has been established for accurately measuring the size of lesions on such an inner wall. In this background, a purpose of the present disclosure is to provide a technique for accurately identifying information on the size of a lesion contained in an image captured by an endoscope.

A shape measurement system for endoscopes according to one aspect of the present disclosure includes one or more processors having hardware, wherein the one or more processors are configured to: display an endoscopic image of a living tissue in a somatic cavity captured by an endoscope on a display device; receive a user operation for setting an area of interest in the endoscopic image; set the area of interest in the endoscopic image based on the user operation; acquire three-dimensional shape information of the living tissue subjected to image capturing by the endoscope; derive three-dimensional shape information of a virtual surface in the area of interest from three-dimensional shape information of an area different from the area of interest; and identify information concerning a size of the virtual surface from the three-dimensional shape information of the virtual surface. The shape measurement system for endoscopes may have a plurality of processors, and the plurality of processors may cooperate to perform the above process.

A shape measurement method for endoscopes according to another aspect of the present disclosure includes: displaying an endoscopic image of a living tissue in a somatic cavity captured by an endoscope on a display device; receiving a user operation for setting an area of interest in the endoscopic image; setting the area of interest in the endoscopic image based on the user operation; acquiring three-dimensional shape information of the living tissue subjected to image capturing by the endoscope; deriving three-dimensional shape information of a virtual surface in the area of interest from three-dimensional shape information of an area different from the area of interest; and identifying information concerning a size of the virtual surface from the three-dimensional shape information of the virtual surface.

Optional combinations of the aforementioned constituting elements and implementations of the present disclosure in the form of methods, apparatuses, systems, recording mediums, and computer programs may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 1A shows an example of an image captured by an endoscope; and FIG. 1B schematically shows a situation at the time of endoscopic image capturing;

FIG. 3 is a diagram showing functional blocks in the shape measurement system for endoscopes;

DETAILED DESCRIPTION

The disclosure will now be described by reference to the preferred embodiments. This does not intend to limit the scope of the present disclosure, but to exemplify the disclosure.

Figures 1A, 1B:
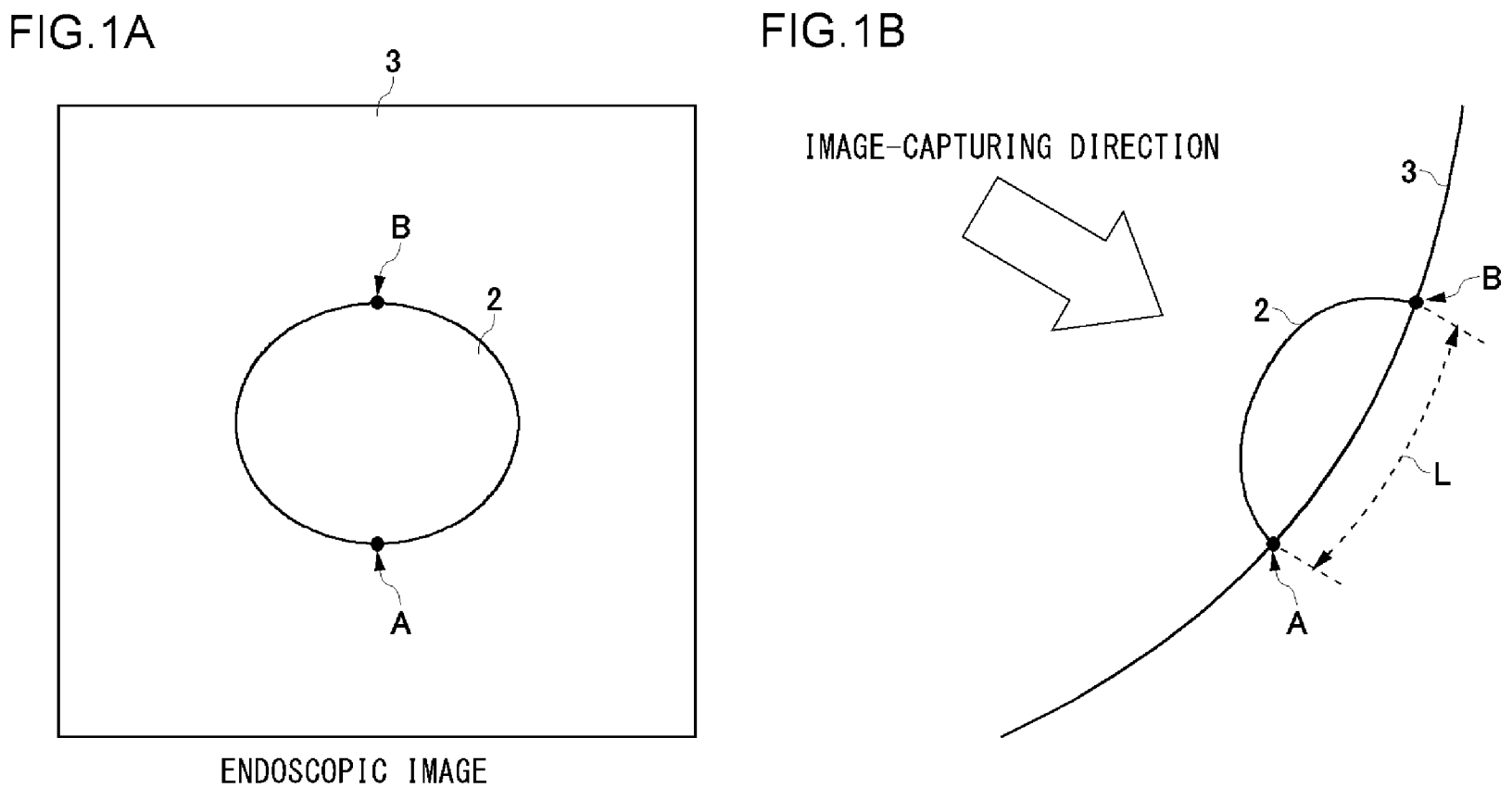

FIG. 1 shows an example of an image of living tissue in a somatic cavity captured by an endoscope. In this endoscopic image, a lesion 2 is included in a central area, and a biological surface 3, which is the inner wall surface of the digestive tract, is included around the lesion 2. FIG. 1B schematically shows a situation at the time of endoscopic image capturing. In this example, the lesion 2 is a tumor that rises from the curved biological surface 3. However, there are some lesions 2 that are recessed from the biological surface 3.

Since the biological surface 3 has a curved shape, the length L between points A and B in the lesion 2 is not the length of a line segment connecting the points A and B with a straight line but the length along the curved biological surface 3. Since the endoscopic image does not include the biological surface 3 that is hidden by the lesion 2, the size of the lesion 2 is measured by estimating the three-dimensional shape of the biological surface 3 (hereinafter referred to as "virtual surface") hidden by the lesion 2 in an embodiment.

Figure 2:
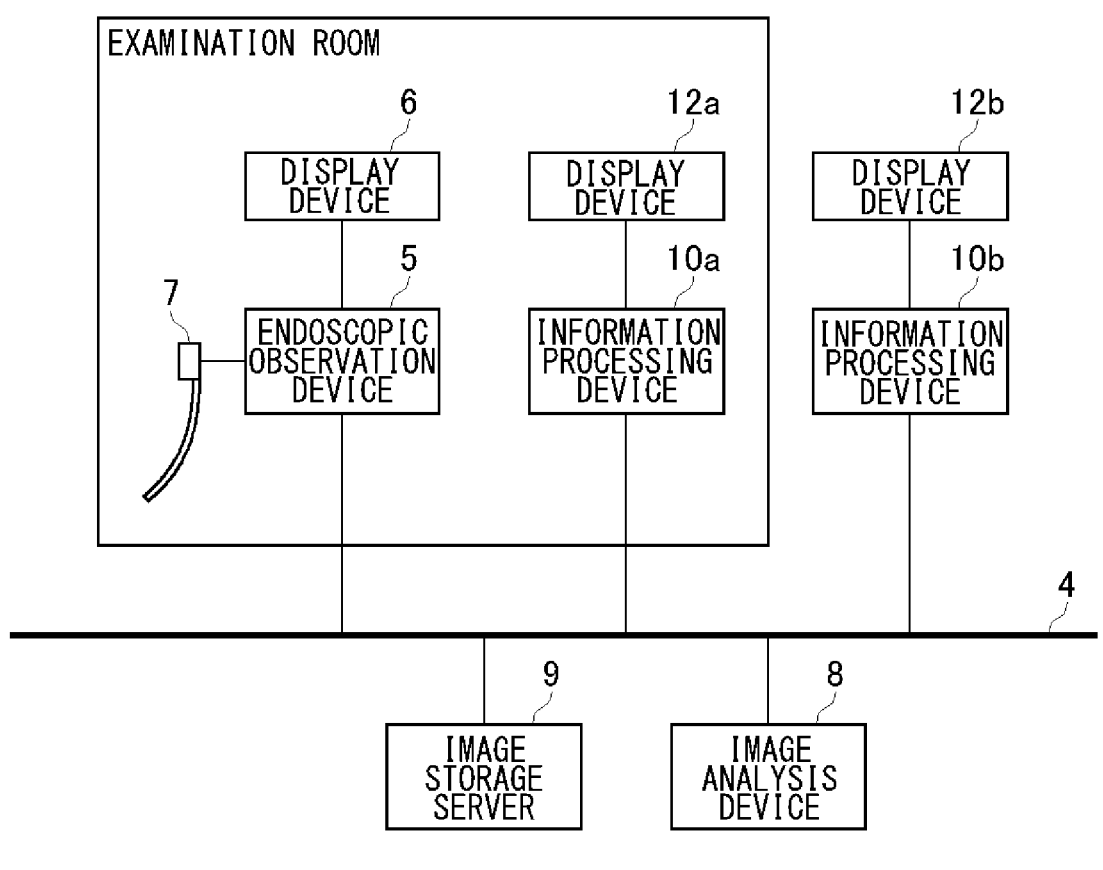
FIG. 2 is a diagram showing the configuration of a shape measurement system for endoscopes.

FIG. 2 shows the configuration of a shape measurement system 1 for endoscopes according to the embodiment. The shape measurement system 1 for endoscopes is provided in a medical facility such as a hospital where endoscopic examinations are performed. In the shape measurement system 1 for endoscopes, an endoscopic observation device 5, an information processing device 10a, an information processing device 10b, and an image analysis device 8 are communicatively connected via a network 4 such as a local area network (LAN).

The endoscopic observation device 5 is provided in an examination room and is connected to an endoscope 7 to be inserted into the digestive tract of a patient. The endoscope 7 has a light guide for illuminating the inside of the digestive tract by transmitting illumination light supplied from the endoscopic observation device 5, and the distal end of the endoscope 7 is provided with an illumination window for emitting the illumination light transmitted by the light guide to living tissue and an image-capturing unit for image-capturing the living tissue at a predetermined cycle and outputting an image-capturing signal to the endoscopic observation device 5. The endoscopic observation device 5 supplies illumination light according to the observation mode to the endoscope 7. The image-capturing unit includes a solid-state imaging device, for example, a CCD image sensor or a CMOS image sensor, that converts incident light into an electric signal.

The endoscopic observation device 5 performs image processing on the image-capturing signal photoelectrically converted by a solid-state imaging device of the endoscope 7 so as to generate an endoscopic image and displays the endoscopic image on the display device 6 in real time. In addition to normal image processing such as A/D conversion and noise removal, the endoscopic observation device 5 may include a function of performing special image processing for the purpose of highlighting, etc. When the endoscopic observation device 5 is equipped with a special image processing function, the endoscopic observation device 5 can generate an endoscopic image that has not undergone special image processing and an endoscopic image that has undergone the special image processing from an image-capturing signal resulting from image capturing using the same illumination light.

In the embodiment, endoscopic images may be white light imaging (WLI) observation images generated from image-capturing signals resulting from image capturing using normal light (white light), texture and color enhancement imaging (TXI) observation images generated by applying special image processing to image-capturing signals resulting from image capturing using normal light, RDI observation images generated from image-capturing signals resulting from image capturing using special light, narrow band imaging (NBI) observation images, and autofluorescence imaging (AFI) observation images. The endoscopic images may be pseudo-color images of the unevenness of a subject or other images generated by image processing of image-capturing signals from the endoscope 7.

According to the examination procedure, the doctor observes an endoscopic image displayed on the display device 6. When the doctor operates the release switch of the endoscope 7, the endoscopic observation device 5 captures or saves an endoscopic image at the time when the release switch is operated and transmits the captured endoscopic image to an image storage server 9. The endoscopic images stored in the image storage server 9 are used by the doctor to create an examination report.

The information processing device 10a is installed in an examination room and is used by users such as doctors and nurses to check information on the size of lesions contained in endoscopic images in real time during endoscopic examinations. The information processing device 10a may cooperate with the image analysis device 8 so as to provide the user with information on the size of the lesions.

The information processing device 10b is installed in a room other than the examination room and is used by a doctor to prepare an examination report. For example, a lesion shape measurement function of the information processing device 10b may be used by the doctor in order to check whether a lesion subjected to image capturing in the current detailed examination is large enough to be subject to ESD in the next examination. Once the doctor confirms that the lesion subjected to image capturing is large enough to be subject to ESD, the doctor may decide to resect the lesion en bloc using ESD at the next endoscopic examination.

The image analysis device 8 is provided with an image analysis function of detecting a lesion and outputting an area where the lesion exists, a lesion area, when an endoscopic image is input. The image analysis device 8 may use a trained model that is generated by machine learning using endoscopic images for training and information concerning a lesion area contained in the endoscopic images as training data and that outputs the position of the lesion area when an endoscopic image is input. During an endoscopic examination, the image analysis device 8 may be provided with endoscopic images from the endoscopic observation device 5 and may supply image analysis results to the endoscopic observation device 5 or the information processing device 10a.

FIG. 3 shows functional blocks in the shape measurement system 1 for endoscopes. The shape measurement system 1 for endoscopes includes a processing device 20 that executes a lesion shape measurement process, a trained model holding unit 60, and a user interface 70. The processing device 20 has an operation reception unit 30, an area setting unit 32, a three-dimensional information acquisition unit 38, an image generation unit 40, an image analysis unit 42, an auxiliary information generation unit 44, a display processing unit 46, a virtual surface derivation unit 48, and a size information identification unit 50, while the area setting unit 32 has an area-of-interest setting unit 34 and a reference area setting unit 36. The user interface 70 is a tool for the user to input operations, such as a mouse, a stylus, or a keyboard, for example.

The configuration shown in FIG. 3 is implemented by hardware such as an arbitrary processor, memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

The functional blocks of the shape measurement system 1 for endoscopes shown in FIG. 3 are realized by at least one of the following devices: the endoscopic observation device 5, the information processing device 10a, the information processing device 10b, and the image analysis device 8. The functional blocks of the shape measurement system 1 for endoscopes may be realized by each of the endoscopic observation device 5, the information processing device 10a, the information processing device 10b, and the image analysis device 8 alone, or by a combination of two or more devices. Therefore, the functional block shown as the processing device 20 may be realized by one or more processors in a single device or may be realized by a plurality of processors included in two or more devices.

During an endoscopic examination, the endoscopic observation device 5 displays an image of the inside of the digestive tract being captured by the endoscope 7 on the display device 6. The doctor observes the endoscopic image displayed on the display device 6 while moving the endoscope 7, and when a lesion appears on the display device 6, the doctor operates the release switch of the endoscope 7. The endoscopic observation device 5 captures an endoscopic image at the time when the release switch is operated and transmits the captured endoscopic image to the image storage server 9 along with information identifying the endoscopic image (image ID). The endoscopic observation device 5 may transmit a plurality of captured endoscopic images together to the image storage server 9 after the examination is completed. The image storage server 9 records the endoscopic images transmitted from the endoscopic observation device 5 in association with an examination ID for identifying the endoscopic examination.

The endoscopic observation device 5 in the embodiment has a function of measuring three-dimensional shape information of living tissue contained in a captured endoscopic image. The endoscopic observation device 5 may measure the three-dimensional shape of the living tissue subjected to image capturing, using a known technique. The endoscopic observation device 5 measures the three-dimensional shape of the living tissue contained in the captured endoscopic image, adds the measured three-dimensional shape information to the endoscopic image, and transmits the endoscopic image to the image storage server 9. Therefore, the image storage server 9 records the endoscopic image in association with the three-dimensional shape information of the captured living tissue.

For example, the endoscope 7 may be equipped with a stereo camera, and the endoscopic observation device 5 may measure the three-dimensional shape of the living tissue using the principle of triangulation from images captured by the two cameras. The endoscopic observation device 5 may also project a projected image of a measurement pattern using a laser beam onto the living tissue and measure the three-dimensional shape of the living tissue based on the image-capturing result of the measurement pattern projected onto the living tissue, as in the disclosure of Japanese Patent Application Publication No. 2017-23562A. The endoscopic observation device 5 may also measure the three-dimensional shape of the living tissue from an endoscopic image captured by a monocular camera, using a trained model that has been machine-learned as training data using an image acquired by the stereo camera and the distance information of the living tissue contained in the image. Alternatively, the endoscopic observation device 5 may measure the three-dimensional shape of the living tissue based on the inter-frame feature value of the endoscopic image captured by the monocular camera. As described, the endoscopic observation device 5 uses a known measurement technique so as to measure the three-dimensional shape of the living tissue in an endoscopic image.

The three-dimensional shape measurement function for living tissue subjected to image capturing may be installed in a device other than the endoscopic observation device 5. For example, the three-dimensional shape measurement function may be installed in the information processing device 10a, in the image analysis device 8, or in the image storage server 9. Although any device may measure the three-dimensional shape of the living tissue, the image storage server 9 records the endoscopic image transmitted from the endoscopic observation device 5 in association with the three-dimensional shape information of the captured living tissue or data for calculating the three-dimensional shape information.

After the examination is completed, the doctor operates the information processing device 10b so as to create an examination report. The information processing device 10b reads endoscopic images captured during the examination from the image storage server 9 and displays the endoscopic images on the display device 12b, and the doctor diagnoses a lesion included in the displayed endoscopic images. When there is a request from the doctor, the information processing device 10b according to the embodiment derives the three-dimensional shape of a biological surface (virtual surface) hidden by the lesion included in the endoscopic images and performs a process of identifying the size of the virtual surface, i.e., the size of the lesion bottom surface. The following is an explanation of a case in which the information processing device 10b realizes the lesion shape measurement function of the processing device 20 (see FIG. 3).

Figure 4:
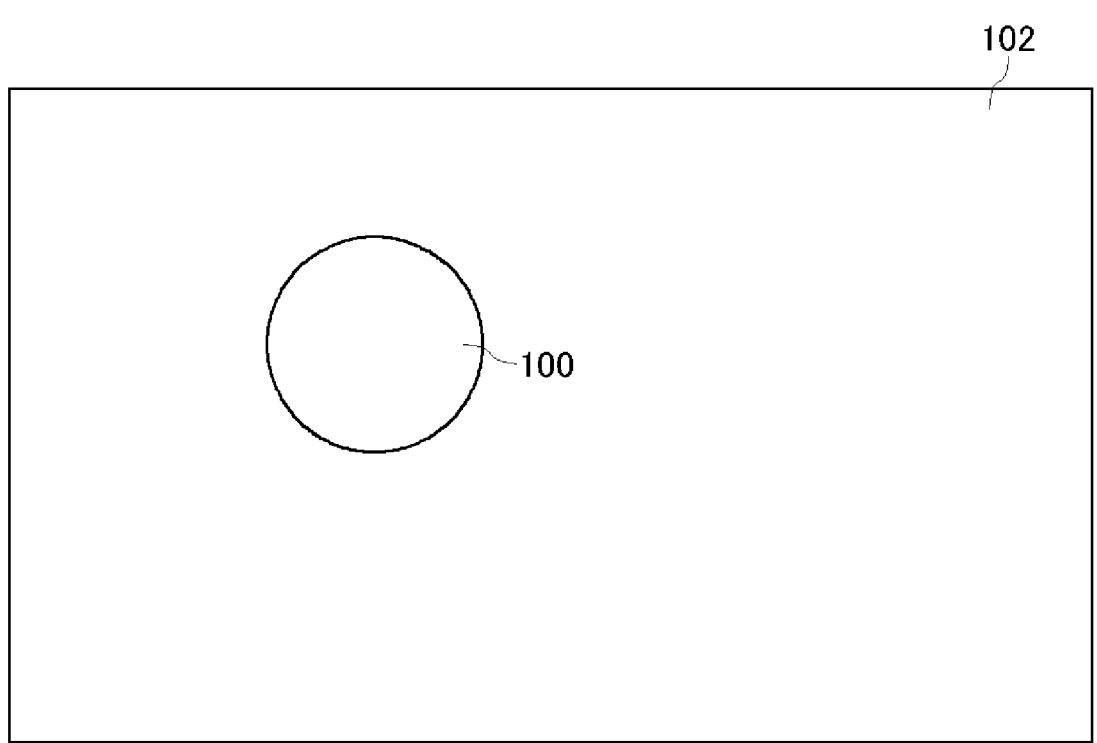
FIG. 4 is a diagram showing an example of an endoscopic image.

FIG. 4 shows an example of an endoscopic image displayed on the display device 12b. The display processing unit 46 acquires an endoscopic image associated with the examination ID of the examination for which a report is to be generated from the image storage server 9 and displays the endoscopic image on the display device 12b. The endoscopic image is an image of the living tissue in the somatic cavity captured by the endoscope 7. The endoscopic image shown in FIG. 4 includes a substantially circular lesion 100 and a surrounding biological surface 102, which is the inner wall surface of the digestive tract.

Figure 5:
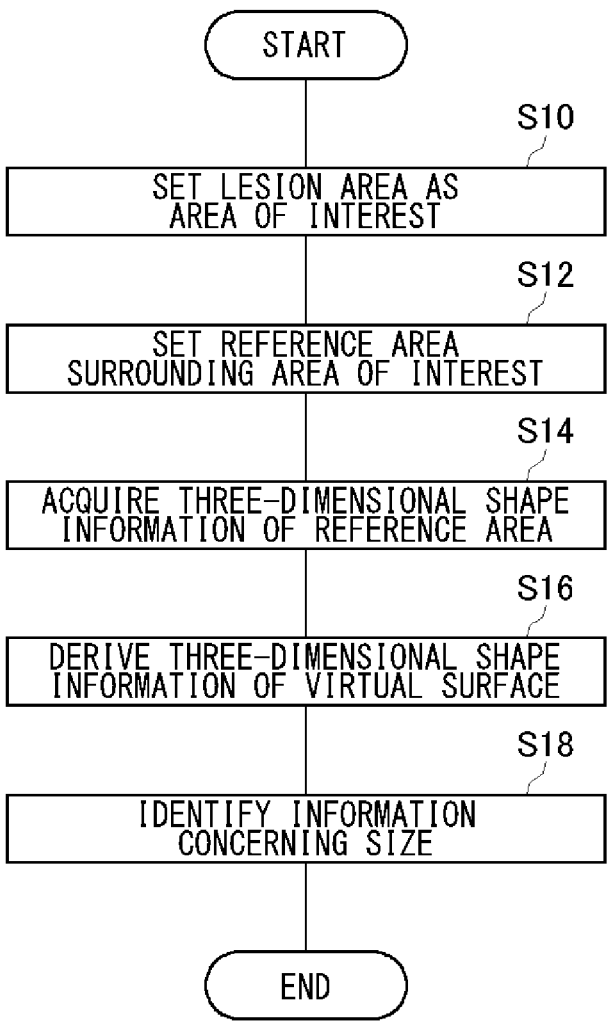
FIG. 5 is a diagram showing a flowchart of a lesion shape measurement process.

FIG. 5 shows a flowchart of the lesion shape measurement process. The user, who is a doctor, operates the user interface 70 so as to set an area of interest in an endoscopic image displayed on the display device 12b (S10).

Figure 6:
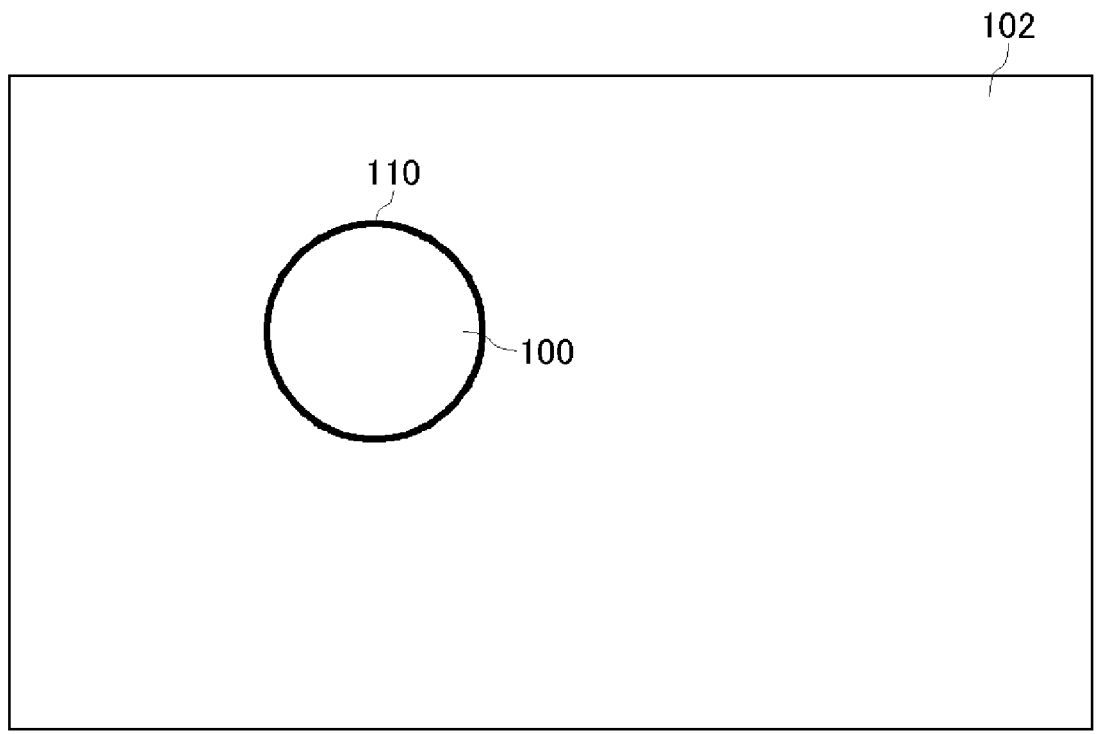
FIG. 6 is a diagram showing an example of an area of interest that has been set.

FIG. 6 shows an example of an area of interest 110 that has been set. The user operates the user interface 70 such as a mouse so as to draw a boundary line at the border between a lesion 100 and the biological surface 102 in the endoscopic image displayed on the display device 12b. When the operation reception unit 30 receives a user operation for setting an area of interest in the endoscopic image, the area-of-interest setting unit 34 sets the area of interest 110 in the endoscopic image based on the user operation. The area of interest 110 is a lesion area surrounded by a boundary line. Since the user, who is a doctor, can recognize the boundary between the lesion 100 and the biological surface 102 based on medical findings such as three-dimensional shape and color tone characteristics, the area-of-interest setting unit 34 can accurately set the area of interest 110 indicating the lesion area based on the user operation.

After the area-of-interest setting unit 34 sets the area of interest 110, the reference area setting unit 36 sets a reference area surrounding the area of interest 110 based on the area of interest 110 (S12). The reference area 120 is set to encompass at least all of the area of interest 110 and to be larger than the area of interest 110. By setting the reference area by the reference area setting unit 36, the virtual surface derivation unit 48 can derive the three-dimensional shape information of the virtual surface with high accuracy even when the biological surface has a complex curved shape as described below.

Figure 7:
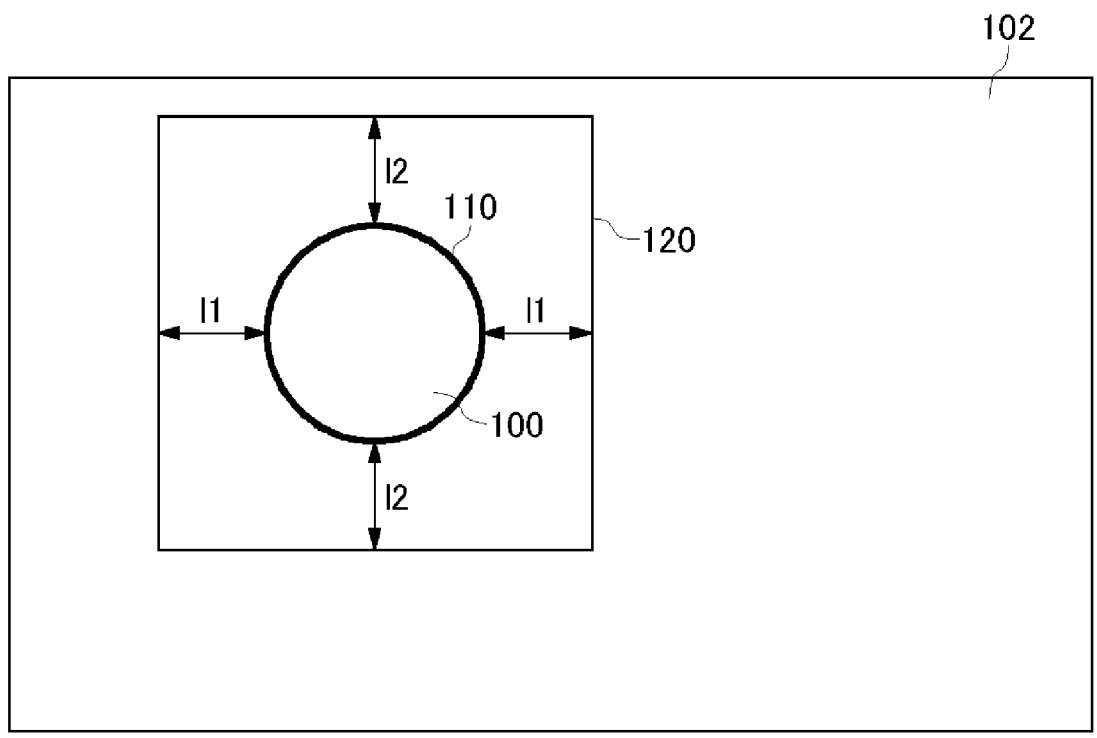
FIG. 7 is a diagram showing a reference area that has been set.

FIG. 7 shows an example of a reference area 120 that has been set. The reference area setting unit 36 preferably sets the reference area 120 such that the reference area 120 has a margin of a predetermined length or longer outside the outer edge of the area of interest 110. For example, as the reference area 120, the reference area setting unit 36 may set a rectangular area consisting of left and right edges passing through positions that are a predetermined length 11 away from the leftmost and rightmost edges of the area of interest 110, respectively, and top and bottom edges passing through positions that are a predetermined length 12 away from the uppermost and lowermost edges of the area of interest 110, respectively.

The user may set the reference area 120 to the area of interest 110 displayed on the display device 12b by operating the user interface 70. When the operation reception unit 30 receives a user operation for setting a reference area in the endoscopic image, the reference area setting unit 36 sets the reference area 120 in the endoscopic image based on the user operation. Since the reference area 120 to be set defines the range of three-dimensional shape information to be used in deriving the virtual surface of the area of interest 110, the user preferably determines as the reference area 120 the range in which the virtual surface of the area of interest 110 can be suitably derived.

After the reference area setting unit 36 sets the reference area 120, the three-dimensional information acquisition unit 38 acquires the three-dimensional shape information of the living tissue subjected to image capturing by the endoscope (S14). As described above, the three-dimensional shape information of the living tissue is recorded on the image storage server 9 in association with the endoscopic image, and the three-dimensional information acquisition unit 38 acquires the three-dimensional shape information associated with the endoscopic image.

A virtual surface derivation unit 48 derives three-dimensional shape information of a virtual surface in the area of interest 110 from three-dimensional shape information of an area different from the area of interest 110 (S16). The three-dimensional shape information of the virtual surface may include two-dimensional coordinates of each pixel on the virtual surface in the endoscopic image and distance information (depth information) of each pixel. More specifically, the virtual surface derivation unit 48 derives three-dimensional shape information of the virtual surface in the area of interest 110 from the three-dimensional shape information of the reference area 120. As shown in FIG. 1, the virtual surface in the area of interest 110 means a virtual biological surface (biological surface 102 when it is assumed that the lesion 100 does not exist) that exists on the back side of the lesion 100.

Figure 8:
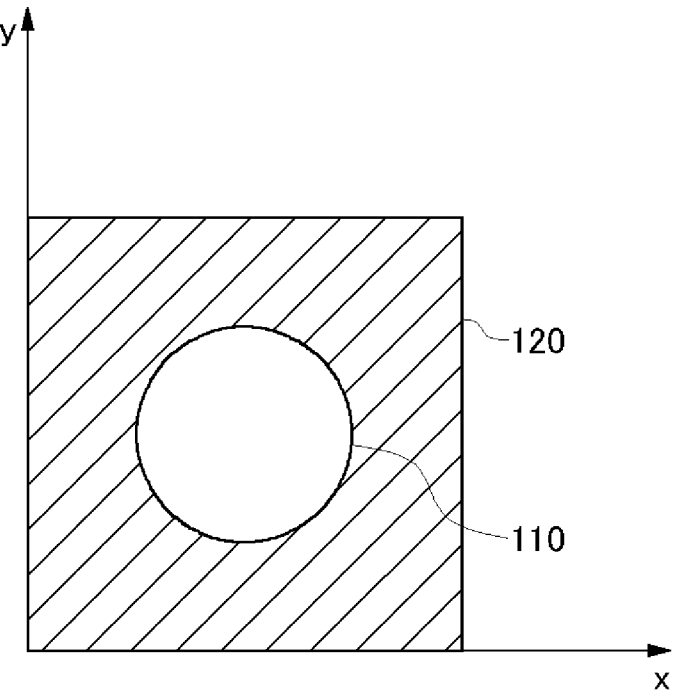
FIG. 8 is a diagram showing a state where the reference area is arranged in an xy-plane.

FIG. 8 shows a state where the reference area 120 is arranged in an xy-plane. In FIG. 8, the position of an endoscopic image in the horizontal direction is represented by an x-coordinate and the position in the height direction is represented by a y-coordinate. Of the three-dimensional information of each pixel, the position in the direction of distance from the camera (depth position) may be represented by a z-coordinate. In FIG. 8, the hatched area indicates the reference area 120 in the xy-plane, and the virtual surface derivation unit 48 derives the three-dimensional shape information of the virtual surface in the area of interest 110 from the three-dimensional shape information of the reference area 120. When deriving the three-dimensional shape information of the virtual surface, the virtual surface derivation unit 48 does not use the three-dimensional shape information of the area of interest 110.

Figure 9A:
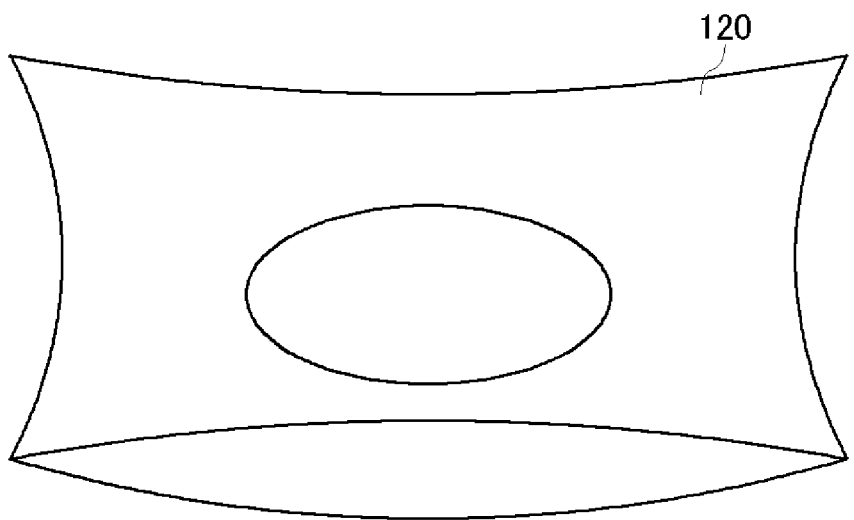
FIG. 9A and FIG. 9B are diagrams showing examples of a three-dimensional shape of the reference area.
Figure 9B:
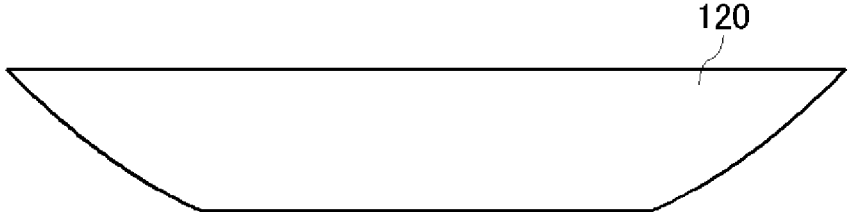

FIG. 9 shows an example of the three-dimensional shape of the reference area 120. FIG. 9A is a perspective view of the three-dimensional shape of the reference area 120, and FIG. 9B is a view of the three-dimensional shape of the reference area 120 viewed in the y-axis direction.

Figure 10:
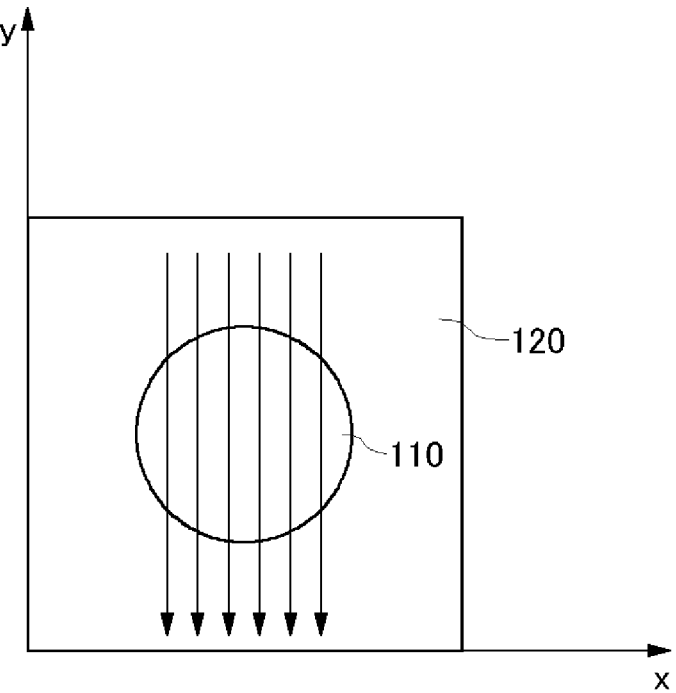
FIG. 10 is a diagram for explaining a technique for deriving the three-dimensional shape of a virtual surface.

FIG. 10 is a diagram for explaining a technique for deriving the three-dimensional shape of a virtual surface in the area of interest 110. The virtual surface derivation unit 48 performs a fitting process for the three-dimensional shape of the area of interest 110 from the three-dimensional shape information of the reference area 120 for each column in the y-axis direction with a predetermined interval in the x-axis direction. More specifically, as shown in FIG. 10, a polynomial approximation curve is obtained from three-dimensional point cloud data in the reference area 120 for each column extending in the y-axis direction. The virtual surface derivation unit 48 divides the area of interest 110 into N evenly spaced divisions in the x-axis direction and derives a polynomial approximation curve that fits each division line (column). Then, the virtual surface derivation unit 48 may also perform the fitting process in the x-axis direction based on the point cloud data of the N polynomial approximation curves so as to derive the three-dimensional shape information of a smooth virtual surface. In this way, the virtual surface derivation unit 48 can derive the three-dimensional shape information of the virtual surface with high accuracy even if the biological surface has a complicated curved shape by using the reference area 120 set by the reference area setting unit 36.

Figure 11A:
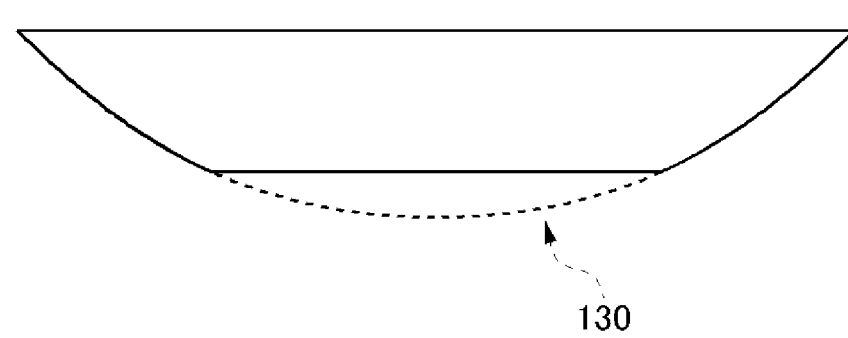
FIG. 11A and FIG. 11B are diagrams showing the derived three-dimensional shape of the virtual surface.
Figure 11B:
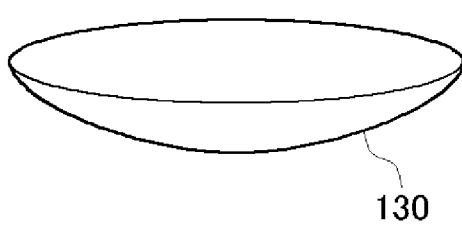

FIG. 11A shows an example of a virtual surface 130 derived for the three-dimensional shape of the reference area 120 shown in FIG. 9B, and FIG. 11B shows an example of the three-dimensional shape of the derived virtual surface 130. The virtual surface derivation unit 48 according to the embodiment performs the fitting process for the three-dimensional shape for deriving a polynomial approximation curve. Alternatively, the virtual surface derivation unit 48 may perform other types of fitting processes. The virtual surface derivation unit 48 according to the embodiment derives the virtual surface 130 in the area of interest 110 by smoothly making a connection in an empty space in the center of the three-dimensional shape of the reference area 120. The virtual surface 130 thus generated corresponds to the virtual bottom surface of the lesion 100 in the area of interest 110.

The size information identification unit 50 identifies information concerning the size of the virtual surface 130 from the three-dimensional shape information of the virtual surface 130 (S18). For example, the size information identification unit 50 may derive the maximum diameter and minimum diameter of the virtual surface 130 as follows.

Figures 12A, 12B, 12C:
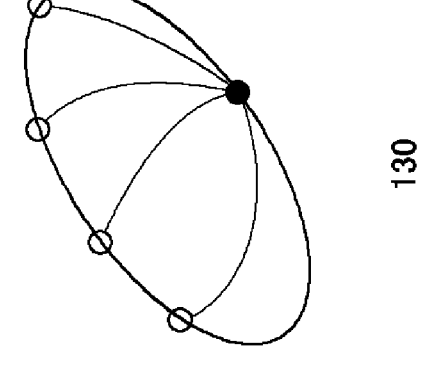
FIG. 12A to FIG. 12C are diagrams for explaining a technique for calculating the size of the virtual surface.

FIG. 12A is a diagram for explaining a technique for calculating the maximum diameter of the virtual surface 130. The size information identification unit 50 calculates the path distance along the virtual surface 130 between any two points on the boundary and identifies the maximum value of the path distance as the maximum diameter.

FIG. 12B shows the combination of two points with the maximum path distance. When the size information identification unit 50 determines that the path distance between points P and Q on the boundary is the maximum, the size information identification unit 50 identifies the path distance between the points P and Q as the "maximum diameter" of the virtual surface 130. Once the maximum diameter is identified, the size information identification unit 50 derives the combination of two points that has the largest path distance among the paths orthogonal to the path of the maximum diameter.

FIG. 12C shows the combination of two points with the maximum path distance in the direction intersecting the maximum diameter. When the size information identification unit 50 determines that the path distance between points R and S on the boundary is the maximum, the size information identification unit 50 identifies the path distance between the points R and S as the "minimum diameter" of the virtual surface 130.

Figure 16:
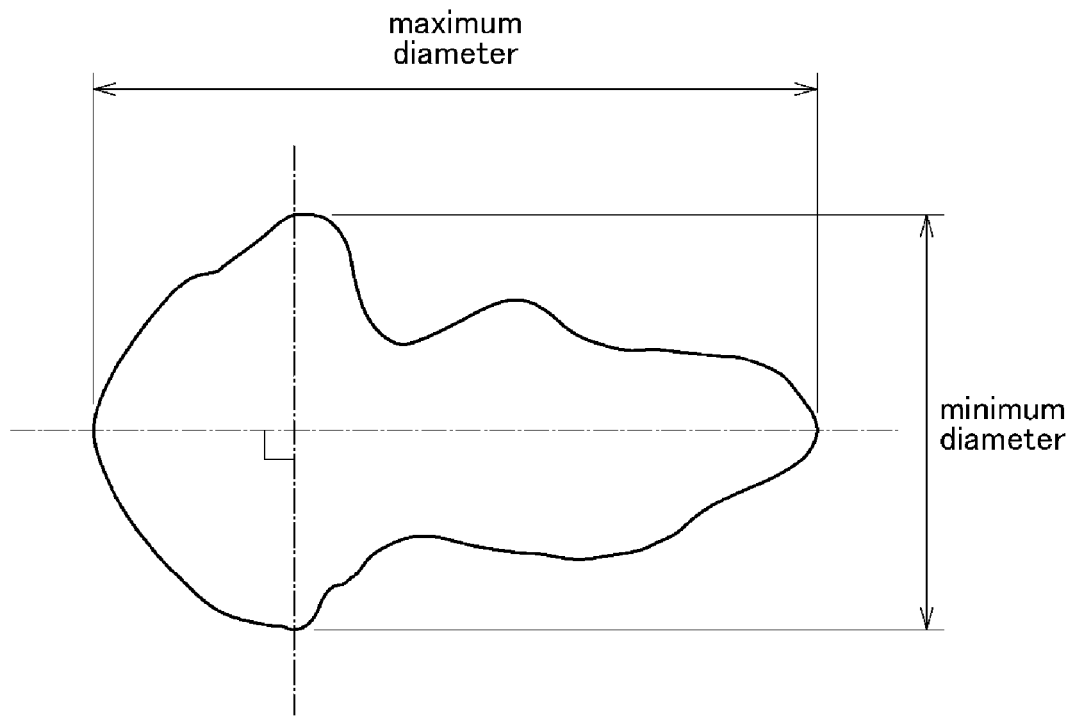
FIG. 16 is a diagram showing the maximum and minimum diameters in two dimensions.

FIG. 16 shows the maximum and minimum diameters in two dimensions. The maximum diameter is identified as the maximum distance of the path between two points on the boundary. The minimum diameter is identified as the maximum distance of the path, which is orthogonal to the path of the maximum diameter, between two points on the boundary.

As described above, the virtual surface 130 corresponds to the virtual bottom surface of the lesion 100, and the size information identification unit 50 derives the maximum and minimum diameters of the bottom surface of the lesion 100 by deriving the maximum and minimum diameters of the virtual surface 130. The display processing unit 46 may display the maximum and minimum diameters of the lesion bottom surface derived by the virtual surface derivation unit 48 on the display device 12b. Learning the maximum and minimum diameters of the lesion bottom surface allows the user to check whether or not the lesion is large enough to be subject to ESD.

The basic step of the lesion shape measurement process is described above. In order to derive the three-dimensional shape information of the virtual surface 130 with high accuracy, an option may be provided for the user to check the process in each step.

Figure 13:
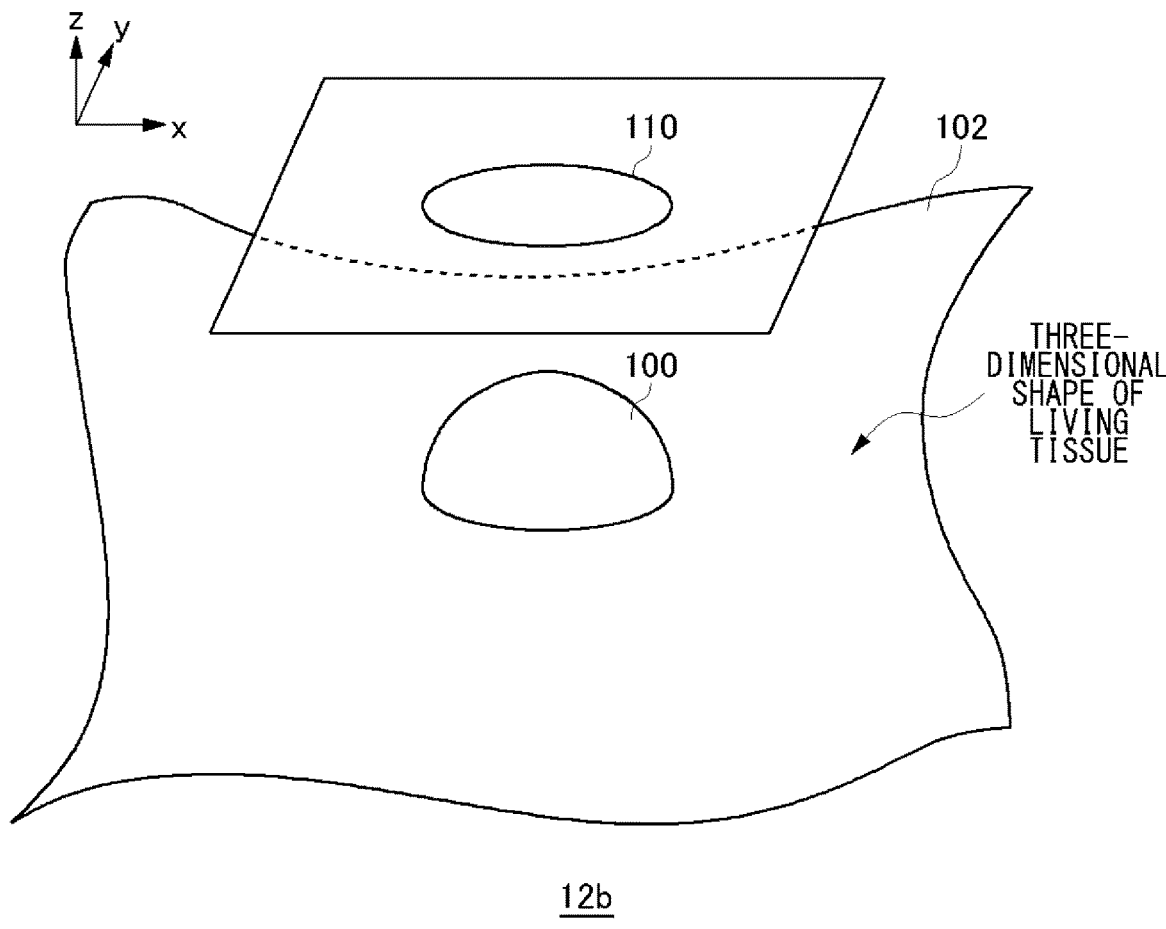
FIG. 13 is a diagram showing an example of a screen for checking the area of interest.

FIG. 13 shows an example of a check screen of an area of interest displayed on the display device 12b. In S10, the user sets the area of interest 110 by operating the user interface 70, and it may be set that the user can check whether the set area of interest 110 is appropriate at this time.

When the user sets the area of interest 110, the image generation unit 40 generates a three-dimensional image of the living tissue based on the three-dimensional shape information of the living tissue. The display processing unit 46 combines the three-dimensional image of the living tissue and the image showing the position of the area of interest 110, and displays the resulting image on the display device 12b. In FIG. 13, the area of interest 110 is synthesized at a position that is distant in the z-axis direction from the three-dimensional image of the living tissue. Alternatively, the area of interest 110 may be synthesized at a position that is aligned in the z-axis direction. When the outer line of the area of interest 110 is superimposed on the three-dimensional image of the living tissue by aligning the position in the z-axis direction, the user can check whether the outer line of the area of interest 110 matches the boundary between the lesion 100 and the biological surface 102. If the outer line does not match the boundary, the user resets the area of interest 110 such that the area of interest 110 matches the area of the lesion 100.

In S12, the display processing unit 46 may combine the three-dimensional image of the living tissue with the image showing the position of the reference area 120, and display the resulting image on the display device 12b. By combining the three-dimensional image of the living tissue with the image showing the position of the reference area 120 and displaying the resulting image, the user can check whether the reference area 120 is set appropriately.

After the virtual surface derivation unit 48 derives the virtual surface 130, the display processing unit 46 may synthesize the virtual surface 130 on the three-dimensional image of the living tissue and display the resulting image on the display device. Although the virtual surface 130 is originally hidden by the lesion 100 and is not visible, by synthesizing the virtual surface 130 on the three-dimensional image of the living tissue, the user can check whether the virtual surface 130 is derived appropriately.

In S16 shown in FIG. 5, the virtual surface derivation unit 48 derives the three-dimensional shape information of the virtual surface 130 from the three-dimensional shape information of the reference area 120, which is different from the area of interest 110; however, there may be an object in the reference area 120 that impairs the continuity of the biological surface. If the virtual surface derivation unit 48 performs the fitting process for the three-dimensional shape of the area of interest 110 based on the three-dimensional shape information of a discontinuous biological surface, the three-dimensional shape information of the virtual surface 130 cannot be estimated with high accuracy.

Figure 14:
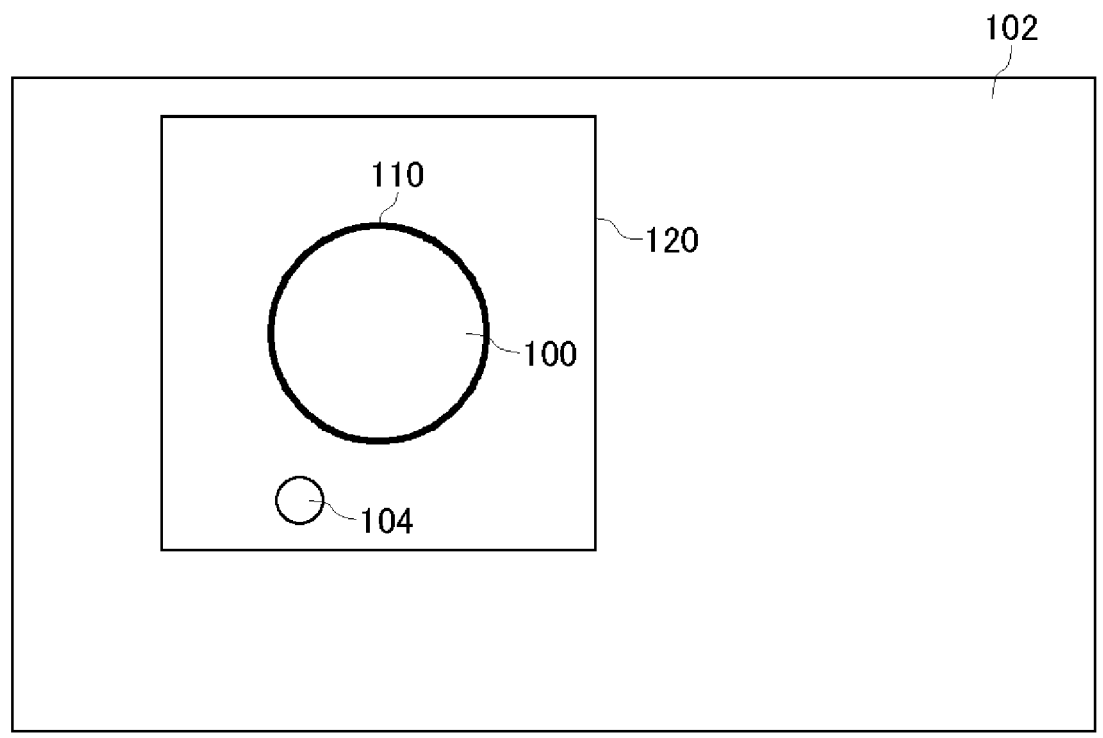
FIG. 14 is a diagram showing an example in which a discontinuity is included in the reference area.

FIG. 14 shows an example in which a discontinuity 104 is included in the reference area 120. The discontinuity 104 is, for example, a convex or concave area that impairs the continuity of the biological surface in the reference area 120 and may be a lesion. When performing the fitting process for the three-dimensional shape, the discontinuity 104 is preferably removed manually by the user before performing fitting process because the discontinuity 104 adversely affects the fitting accuracy.

Figure 15:
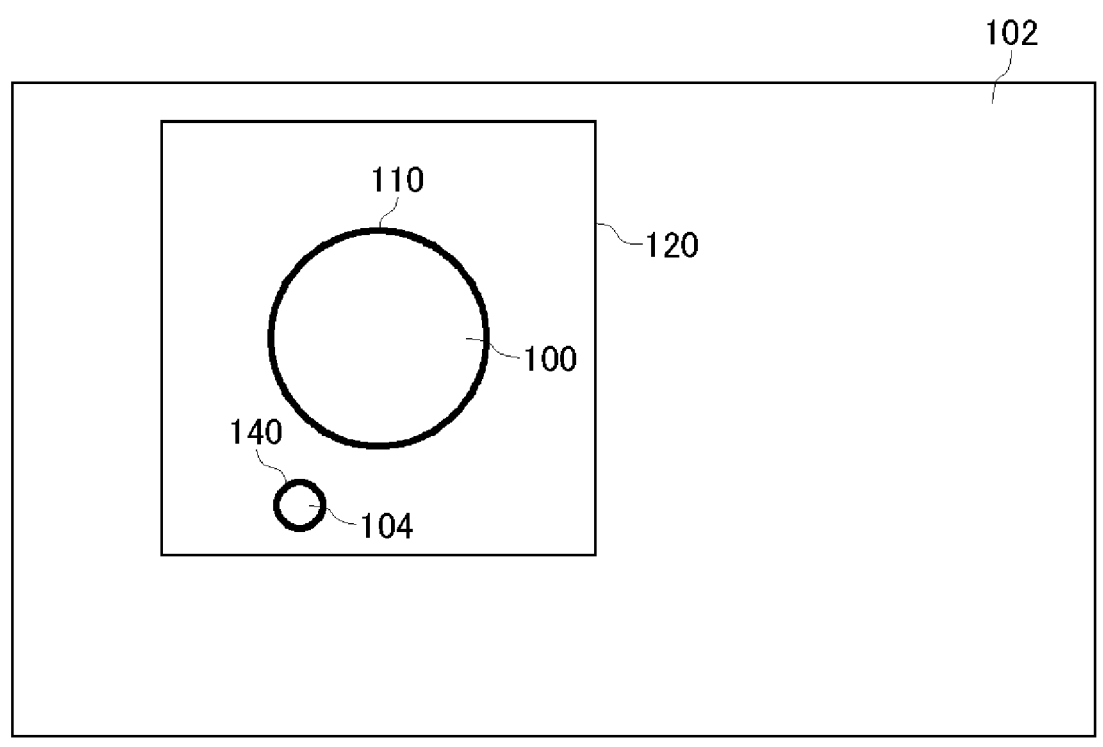
FIG. 15 is a diagram showing an exclusion area that has been set.

FIG. 15 shows an exclusion area 140 that has been set. The user operates the user interface 70 so as to set the exclusion area 140 in an endoscopic image displayed on the display device 12b. When the operation reception unit 30 accepts a user operation for setting the exclusion area 140 in the reference area 120, the virtual surface derivation unit 48 derives the three-dimensional shape information of the virtual surface 130 from the three-dimensional shape information of the reference area 120 excluding the three-dimensional shape information of the exclusion area 140. This allows the virtual surface derivation unit 48 to derive the virtual surface 130 with high accuracy.

At this time, the virtual surface derivation unit 48 may derive a corrected surface (virtual surface) for the exclusion area 140 by performing the fitting process for the three-dimensional shape of the exclusion area 140 from the three-dimensional shape information of the reference area 120 excluding the three-dimensional shape information of the exclusion area 140. In this way, after correcting the three-dimensional shape information of the exclusion area 140, the virtual surface derivation unit 48 may derive the virtual surface 130 of the area of interest 110 from the corrected three-dimensional shape information of the reference area 120.

Described above is an aspect in which the information processing device 10*b* realizes the lesion shape measurement function of the processing device 20 when the user generates an examination report after the examination is completed. As a different aspect, the information processing device 10*a* may cooperate with the image analysis device 8 so as to realize the lesion shape measurement function of the processing device 20 during an endoscopic examination.

The image analysis device 8 has an image analysis unit 42 and a trained model holding unit 60 (see FIG. 3). The trained model holding unit 60 holds a trained model generated by machine learning using endoscopic images for learning and information concerning lesion areas contained in the endoscopic images as training data. This trained model is configured to detect a lesion area upon input of an endoscopic image and to output the position of the lesion area.

During an endoscopic examination, the endoscopic observation device 5 displays an endoscopic image being captured by the endoscope 7 on the display device 6 in real time and transmits the endoscopic image to the information processing device 10*a* and the image analysis device 8. In the image analysis device 8, upon acquiring the endoscopic image, the image analysis unit 42 inputs the endoscopic image to the trained model held in the trained model holding unit 60. When an endoscopic image is input, if the trained model detects a lesion area, the trained model outputs the position information of the lesion area. The image analysis unit 42 transmits the position information of the lesion area output by the trained model to the information processing device 10*a* along with information identifying the endoscopic image (image ID).

In the information processing device 10*a*, the display processing unit 46 displays an endoscopic image being captured by the endoscope 7 on the display device 12*a* and also displays information indicating the position of the lesion area on the endoscopic image based on the position information of the lesion area and the image ID provided by the image analysis device 8. At this time, the display processing unit 46 synchronizes the endoscopic image to be displayed with the information indicating the position of the lesion area to be displayed based on the image ID. For example, as shown in FIG. 6, the display processing unit 46 may superimpose the boundary line of the lesion 100 on the endoscopic image that includes the lesion 100.

When the user operating the information processing device 10*a* confirms that the boundary line of the lesion 100 output by the trained model is correct, the user may decide to set the area of interest 110 by operating the user interface 70. At this time, the operation reception unit 30 receives a user operation for setting an area of interest in the endoscopic image, and the area-of-interest setting unit 34 sets the area of interest in the endoscopic image based on the user operation. When the shape measurement system 1 for endoscopes has a function of detecting the lesion area using the trained model, the area of interest may be set simply by the user confirming that the detected lesion area is correct. Once the area of interest is set, the information processing system 10*a* performs the steps of S12, S14, S16, and S18 shown in FIG. 5 so as to identify information on the size of the virtual surface 130. This information may be provided to the endoscopic observation device 5 and displayed on the display device 6 so as to inform the doctor operating the endoscope 7.

Since the virtual surface derivation unit 48 derives the three-dimensional shape information of the virtual surface 130 from the three-dimensional shape of the surrounding area of the area of interest 110, if the surrounding area is small, it is difficult to derive the three-dimensional shape information of the virtual surface 130 with high accuracy because there is not enough three-dimensional data for estimating the three-dimensional shape of the virtual surface 130. Therefore, the auxiliary information generation unit 44 may generate auxiliary information on the image-capturing range of the endoscope 7 during image capturing based on the position of a lesion area provided by the image analysis device 8. For example, if the percentage of a lesion area in an endoscopic image exceeds a predetermined threshold (e.g., 60%), the auxiliary information generation unit 44 may generate auxiliary information for informing the doctor that the camera of the endoscope 7 is too close to a lesion site since a sufficiently large reference area cannot be secured around the lesion area. The auxiliary information generation unit 44 may provide the generated auxiliary information to the endoscopic observation device 5, and the endoscopic observation device 5 may display the auxiliary information on the display device 6 such that the doctor operating the endoscope 7 can check the auxiliary information. This allows the doctor to recognize that the camera of the endoscope 7 is too close to the lesion site and to move the endoscope 7 such that the camera moves away from the lesion site. Therefore, a peripheral area of a sufficient size is secured around the lesion area, and the virtual surface derivation unit 48 can derive three-dimensional shape information of the virtual surface 130 with high accuracy.

Described above is an explanation on the present disclosure based on the embodiments. These embodiments are intended to be illustrative only, and it will be obvious to those skilled in the art that various modifications to constituting elements and processes could be developed and that such modifications are also within the scope of the present disclosure.

What is claimed is:

1. A shape measurement system for use with an endoscope, the shape measurement system comprising:
   a processor comprising hardware, wherein the processor is configured to:
   display an endoscopic image of a living tissue in a somatic cavity captured by the endoscope on a display device;
   receive a first user operation for setting an area of interest in the endoscopic image;
   set the area of interest in the endoscopic image based on the first user operation;
   acquire three-dimensional shape information of the living tissue captured by the endoscope;
   set a reference area surrounding the area of interest;
   receive a second user operation for setting an exclusion area in the reference area;
   derive three-dimensional shape information of a virtual surface in the area of interest from three-dimensional shape information of the reference area excluding three-dimensional information of the exclusion area; and identify information concerning a size of the virtual surface from the three-dimensional shape information of the virtual surface.

2. The shape measurement system according to claim 1, wherein the processor is configured to:

receive a third user operation for setting the reference area in the endoscopic image; and set the reference area in the endoscopic image based on the third user operation.

3. The shape measurement system according to claim 1, wherein the processor is configured to:

generate a three-dimensional image of the living tissue based on the three-dimensional shape information of the living tissue;

combine the three-dimensional image of the living tissue and the image showing the position of the area of interest; and display the combined three-dimensional image of the living tissue and the image showing the position of the area of interest on the display device.

4. The shape measurement system according to claim 1, wherein the processor is configured to:

generate a three-dimensional image of the living tissue based on the three-dimensional shape information of the living tissue;

combine the three-dimensional image of the living tissue and the image showing the position of the reference area; and display the combined three-dimensional image of the living tissue and the image showing the position of the reference area on the display device.

5. The shape measurement system according to claim 3, wherein the processor is configured to:

combine the virtual surface with the three-dimensional image of the living tissue; and display the combined virtual surface with the three-dimensional image of the living tissue on the display device.

6. The shape measurement system according to claim 1, wherein the processor is configured to:

derive three-dimensional shape information of the virtual surface in the area of interest from three-dimensional shape information of the reference area by performing a fitting process for a three-dimensional shape.

7. The shape measurement system according to claim 1, further comprising:

a trained model that is generated by machine learning using endoscopic images for training and information concerning a lesion area contained in the endoscopic images as training data and that outputs a position of the lesion area when an endoscopic image is input, wherein the processor is configured to:

display information indicating the position of the lesion area output by the trained model.

8. The shape measurement system according to claim 1, further comprising:

a trained model that is generated by machine learning using endoscopic images for training and information concerning a lesion area contained in the endoscopic images as training data and that outputs a position of the lesion area when an endoscopic image is input, wherein the processor is configured to:

generate auxiliary information concerning an image-capturing range of the endoscope during image capturing based on the position of the lesion area output by the trained model; and display the auxiliary information on the display device.

9. The shape measurement system according to claim 1, wherein the processor is configured to:

set the reference area based on the area of interest.

10. A shape measurement method for use with an endoscope, the method comprising:

displaying an endoscopic image of a living tissue in a somatic cavity captured by the endoscope on a display device;

receiving a first user operation for setting an area of interest in the endoscopic image;

setting the area of interest in the endoscopic image based on the user operation;

acquiring three-dimensional shape information of the living tissue captured by the endoscope;

setting a reference area surrounding the area of interest;

receiving a second user operation for setting an exclusion area in the reference area;

deriving three-dimensional shape information of a virtual surface in the area of interest from three-dimensional shape information of the reference area excluding three-dimensional information of the exclusion area; and identifying information concerning a size of the virtual surface from the three-dimensional shape information of the virtual surface.

* * * * *